US011382512B2

(12) United States Patent
Foley et al.

(10) Patent No.: US 11,382,512 B2
(45) Date of Patent: Jul. 12, 2022

(54) ENERGY TRANSFER SYSTEM FOR SPINAL IMPLANTS (71) Applicant: Warsaw Orthopedic, Inc., Warsaw, IN (US)

(72) Inventors: Kevin T. Foley, Germantown, TN (US); Arjun S. Kurian, Memphis, TN (US); Newton Metcalf, Memphis, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 221 days.

(21) Appl. No.: 16/733,643

(22) Filed: Jan. 3, 2020

(65) Prior Publication Data
US 2021/0204814 A1 Jul. 8, 2021

(51) Int. Cl.
A61B 5/00 (2006.01)
A61B 17/70 (2006.01)

(52) U.S. Cl.
CPC .......... *A61B 5/0031* (2013.01); *A61B 5/4566* (2013.01); *A61B 5/4851* (2013.01); *A61B 5/686* (2013.01); *A61B 17/7032* (2013.01); *A61B 2560/0219* (2013.01); *A61B 2562/08* (2013.01)

(58) Field of Classification Search
CPC ... A61B 5/0031; A61B 5/4566; A61B 5/4851; A61B 5/686; A61B 2560/0219
See application file for complete search history.

(56) References Cited

U.S. PATENT DOCUMENTS

| 5,683,432 | A | 11/1997 | Goedeke et al. |
| 6,004,349 | A | 12/1999 | Jackson |
| 6,280,445 | B1 | 8/2001 | Morrison et al. |
| 6,485,491 | B1 | 11/2002 | Farris et al. |
| 8,057,519 | B2 | 11/2011 | Justis et al. |
| 2005/0010221 | A1 | 1/2005 | Dalton |
| 2005/0113081 | A1 | 5/2005 | Tushinsky et al. |
| 2005/0267477 | A1 | 12/2005 | Jackson |
| 2009/0234391 | A1 | 9/2009 | Butler et al. |
| 2010/0201118 | A1 | 8/2010 | Anton et al. |
| 2011/0221569 | A1* | 9/2011 | Hamel ............... G06K 19/0716 340/9.1 |
| 2011/0295159 | A1* | 12/2011 | Shachar .................. A61B 5/45 600/594 |

(Continued)

FOREIGN PATENT DOCUMENTS

WO 2015200720 A2 12/2015

OTHER PUBLICATIONS

International Search Report, PCT/US2019/042516, dated Oct. 31, 2019.

(Continued)

*Primary Examiner* — Daniel L Cerioni
*Assistant Examiner* — Raymond P Dulman
(74) *Attorney, Agent, or Firm* — Fox Rothschild LLP (57) ABSTRACT An energy transfer system includes a spinal implant having one or more antennae, and the spinal implant is configured to be positioned within a spinal area of a patient, and a relay device configured to be positioned within the patient between the implant and the skin of the patient when implanted. The relay device is configured to receive energy from a reader device located externally to the patient and convey at least a portion of the received energy to the one or more antennae of the spinal implant.

14 Claims, 8 Drawing Sheets (56) References Cited

U.S. PATENT DOCUMENTS

2014/0379043 A1   12/2014  Howard
2017/0025888 A1*  1/2017  Cinbis ................ A61N 1/37229
2017/0112436 A1*  4/2017  Hsu .................... A61B 17/7032
2018/0310964 A1   11/2018  Stevenson et al.
2020/0405239 A1*  12/2020  Trabish ................ A61B 5/4023
2021/0205046 A1   7/2021  Metcalf et al.

OTHER PUBLICATIONS

International Search Report, PCT/US2019/042511, dated Oct. 31, 2019.

* cited by examiner

ENERGY TRANSFER SYSTEM FOR SPINAL IMPLANTS

TECHNICAL FIELD

The present disclosure generally relates to a relay system for providing energy to deep tissue implants such as, for example, pedicle screws.

BACKGROUND

Treatment of spinal disorders, such as degenerative disc disease, disc herniations, scoliosis or other curvature abnormalities, and fractures, often requires surgical treatments. For example, spinal fusion may be used to limit motion between vertebral members. As another example, implants may be used to preserve motion between vertebral members.

Surgical treatment typically involves the use of longitudinal members, such as spinal rods. Longitudinal members may be attached to the exterior of two or more vertebral members to assist with the treatment of a spinal disorder. Longitudinal members may provide a stable, rigid column that helps bones to fuse, and may redirect stresses over a wider area away from a damaged or defective region. Also, rigid longitudinal members may help in spinal alignment.

Screw assemblies may be used to connect a longitudinal member to a vertebral member. A screw assembly may include a pedicle screw, hook, or other connector and/or a set screw, among other components. A pedicle screw can be placed in, above and/or below vertebral members that were fused, and a longitudinal member can be used to connect the pedicle screws which inhibits or controls movement. A set screw can be used to secure the connection of a longitudinal member and a pedicle screw, hook or other connector.

Inductive coupling may be used to power and/or communicate with an implant, such as for example, a screw assembly. However, inductive coupling is limited due to distance constraints with an external power source.

SUMMARY

In an embodiment, an energy transfer system includes a spinal implant having one or more antennae, and the spinal implant is configured to be positioned within a spinal area of a patient, and a relay device configured to be positioned within the patient between the implant and the skin of the patient when implanted. The relay device is configured to receive energy from a reader device located externally to the patient and convey at least a portion of the received energy to the one or more antennae of the spinal implant.

The relay device may be configured to receive energy from the reader device when the reader device is placed in proximity to the relay device. The relay device may be configured to receive energy from the reader device when the reader device is placed within two to three inches from the relay device.

The relay device may include an induction coil.

The relay device may be positioned within a subcutaneous pocket.

The implant may be positioned four inches from the skin of the patient.

The relay device may be positioned between a half an inch and three inches from the spinal implant.

The relay device may be positioned between two inches and three inches from the skin of the patient.

The spinal implant may include a pedicle screw having a set screw and an anchoring member. The set screw may include the one or more antennae.

The spinal implant may include a control unit having one or more integrated circuits or micro-electronic chips.

The one or more integrated circuits may include a flexible printed circuit.

The one or more micro-electronic chips may include a radio frequency identification chip, or a near field communication chip.

Optionally, the energy transfer system may include one or more antenna extenders attached to the spinal implant.

The spinal implant may be configured to use the at least a portion of the received energy to power the spinal implant.

The spinal implant may be configured to retrieve data from the received energy.

The relay device may be configured to receive information from the spinal implant and transfer at least a portion of the received information to the reader device.

In an embodiment, an energy transfer system includes a spinal implant having one or more antennae and one or more sensors. The spinal implant is configured to be positioned within a spinal area of a patient. The energy transfer system includes a relay device configured to be positioned within the patient between the implant and the skin of the patient when implanted. The relay device includes memory. The relay device is configured to receive energy from a reader device located externally to the patient and convey at least a portion of the received energy to the one or more antennae of the spinal implant. The spinal implant is configured to transmit data collected by one or more of the sensors to the relay device for storage in the memory.

The relay device may include a battery. The relay device may include a communications device. The one or more sensors may be configured to attach to a longitudinal member of the spinal implant.

DETAILED DESCRIPTION

The exemplary embodiments of the surgical system and related methods of use disclosed are discussed in terms of medical devices for the treatment of musculoskeletal disorders and more particularly, in terms of vertebral fixation screws, including for example pedicle screws, as well as hooks, cross connectors, offset connectors and related systems for use during various spinal procedures or other orthopedic procedures and that may be used in conjunction with other devices and instruments related to spinal treatment, such as rods, wires, plates, intervertebral implants, and other spinal or orthopedic implants, insertion instruments, specialized instruments such as, for example, delivery devices (including various types of cannula) for the delivery of these various spinal or other implants to the vertebra or other areas within a patient in various directions, and/or a method or methods for treating a spine, such as open procedures, mini-open procedures, or minimally invasive procedures. Exemplary prior art devices that may be modified to include the various embodiments of the energy transfer system described in this document and include, for example, U.S. Pat. Nos. 6,485,491 and 8,057,519, all incorporated herein by reference in their entirety.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting.

In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior". Generally, similar spatial references of different aspects or components indicate similar spatial orientation and/or positioning, i.e., that each "first end" is situated on or directed towards the same end of the device. Further, the use of various spatial terminology herein should not be interpreted to limit the various insertion techniques or orientations of the implant relative to the positions in the spine.

The following discussion includes a description of a vertebral pedicle screw system and related components and methods of employing the vertebral pedicle screw in accordance with the principles of the present disclosure. Reference is made in detail to the exemplary embodiments of the present disclosure, which are illustrated in the accompanying figures. Although this disclosure discusses a vertebral pedicle screw as an example of a deep tissue implant, it is understood that other types of implants, such as for example, intervertebral implants, rods, braces, connectors, hooks, plates, and/or the like may be used within the scope of this disclosure.

One or more components of a deep tissue implant (e.g., a pedicle screw system) described herein can be fabricated from biologically acceptable materials suitable for medical applications, including metals, synthetic polymers, ceramics and bone material and/or their composites. For example, the components of an implant, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of an implant may be formed or constructed material composites, including the above materials, to achieve various desired characteristics such as strength, rigidity, elasticity, compliance, biomechanical performance, durability and radiolucency or imaging preference. The components of an implant, individually or collectively, may also be fabricated from a heterogeneous material such as a combination of two or more of the above-described materials. The components of an implant may be monolithically formed, integrally connected or include fastening elements and/or instruments, as described herein. The components of an implant may be formed using a variety of subtractive and additive manufacturing techniques, including, but not limited to machining, milling, extruding, molding, 3D-printing, sintering, coating, vapor deposition, and laser/beam melting. Furthermore, various components of an implant may be coated or treated with a variety of additives or coatings to improve biocompatibility, bone growth promotion or other features. To the extent the plate is entirely or partially radiolucent, it may further include radiographic markers made, for example of metallic pins, at one or both ends, on each corner of the ends, and/or along the length of the implant in various locations including near the center of the assembly.

An implant may be employed, for example, with a minimally invasive procedure, including percutaneous techniques, mini-open and open surgical techniques to deliver and introduce instrumentation and/or one or more implants at a surgical site within a body of a patient, for example, a section of a spine. In some embodiments, an implant may be employed with surgical procedures, as described herein, and/or, for example, corpectomy, discectomy, fusion and/or fixation treatments that employ spinal implants to restore the mechanical support function of vertebrae. In some embodiments, an implant may be employed with surgical approaches, including but not limited to: anterior lumbar interbody fusion (ALIF), direct lateral interbody fusion (DLIF), oblique lateral lumbar interbody fusion (OLLIF), oblique lateral interbody fusion (OLIF), various types of anterior fusion procedures, and any fusion procedure in any portion of the spinal column (sacral, lumbar, thoracic, and cervical, for example). In some embodiments, an implant may be employed with posterior lumbar interbody fusion (PLIF), midline posterior techniques, posterolateral techniques, and/or other posterior techniques. In some embodiments, an implant may be employed for the treatment of spinal disease and/or deformity conditions including, without limitation, scoliosis, spondylolisthesis, and/or the like.

Figure 1:
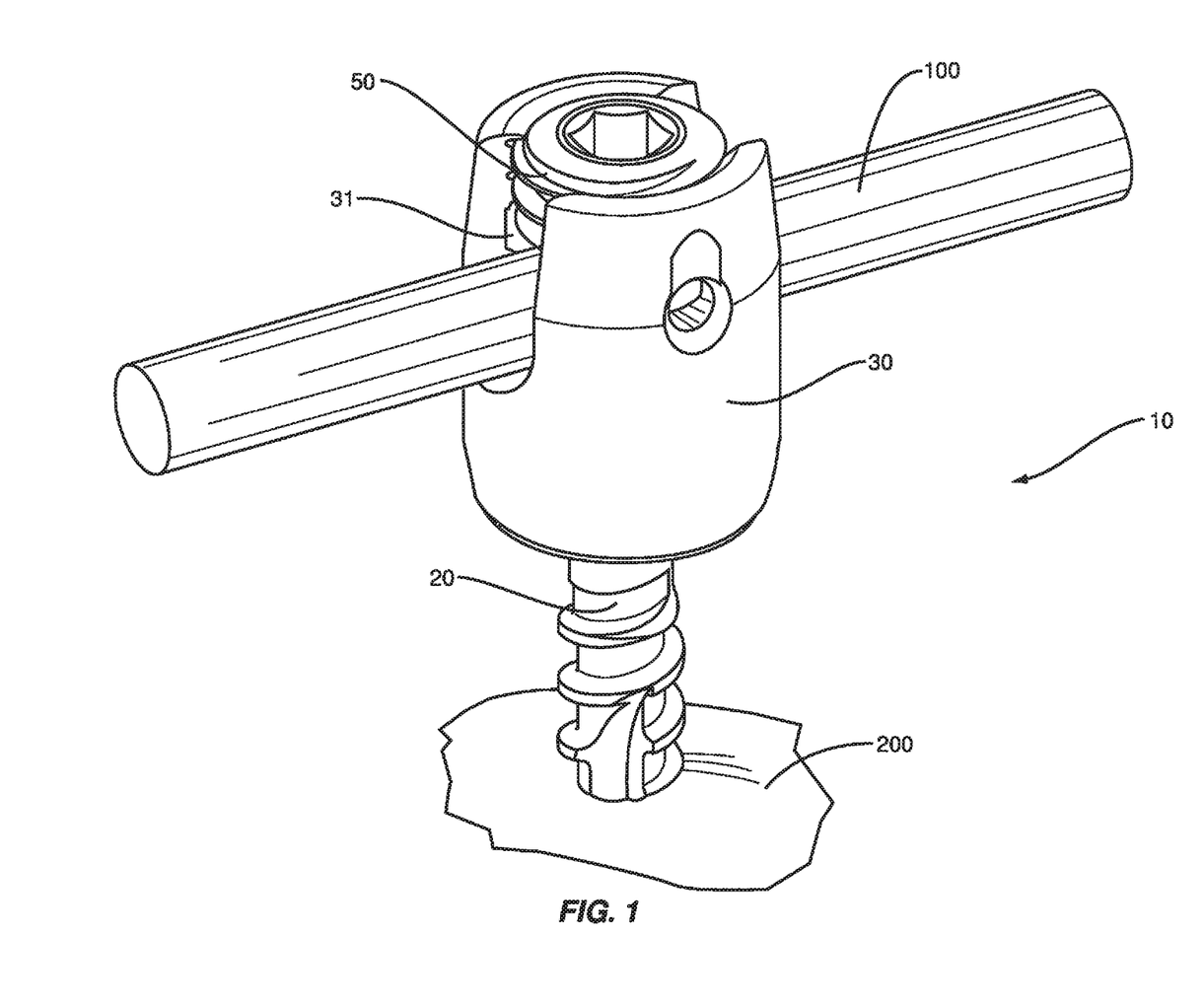
FIG. 1 illustrates an example anchoring assembly and longitudinal member.

FIG. 1 illustrates an example implant 10 having an anchoring assembly and longitudinal member according to an embodiment. As illustrated in FIG. 1, an anchoring assembly includes a screw 20 and an anchoring member 30. The screw 20 has an elongated shape with a first end mounted within a vertebral member 200 and a second end extending outward above the vertebral member 200. The anchoring member 30 is configured to operatively connect to the second end of the screw 20 and is movably connected to the screw 20 to accommodate the longitudinal member 100 positioned at various angular positions. The anchoring member 30 includes a channel 31 sized to receive the longitudinal member 100. A set screw 50 attaches to the anchoring member 30 to capture the longitudinal member 100 within the channel 31.

Figure 2:
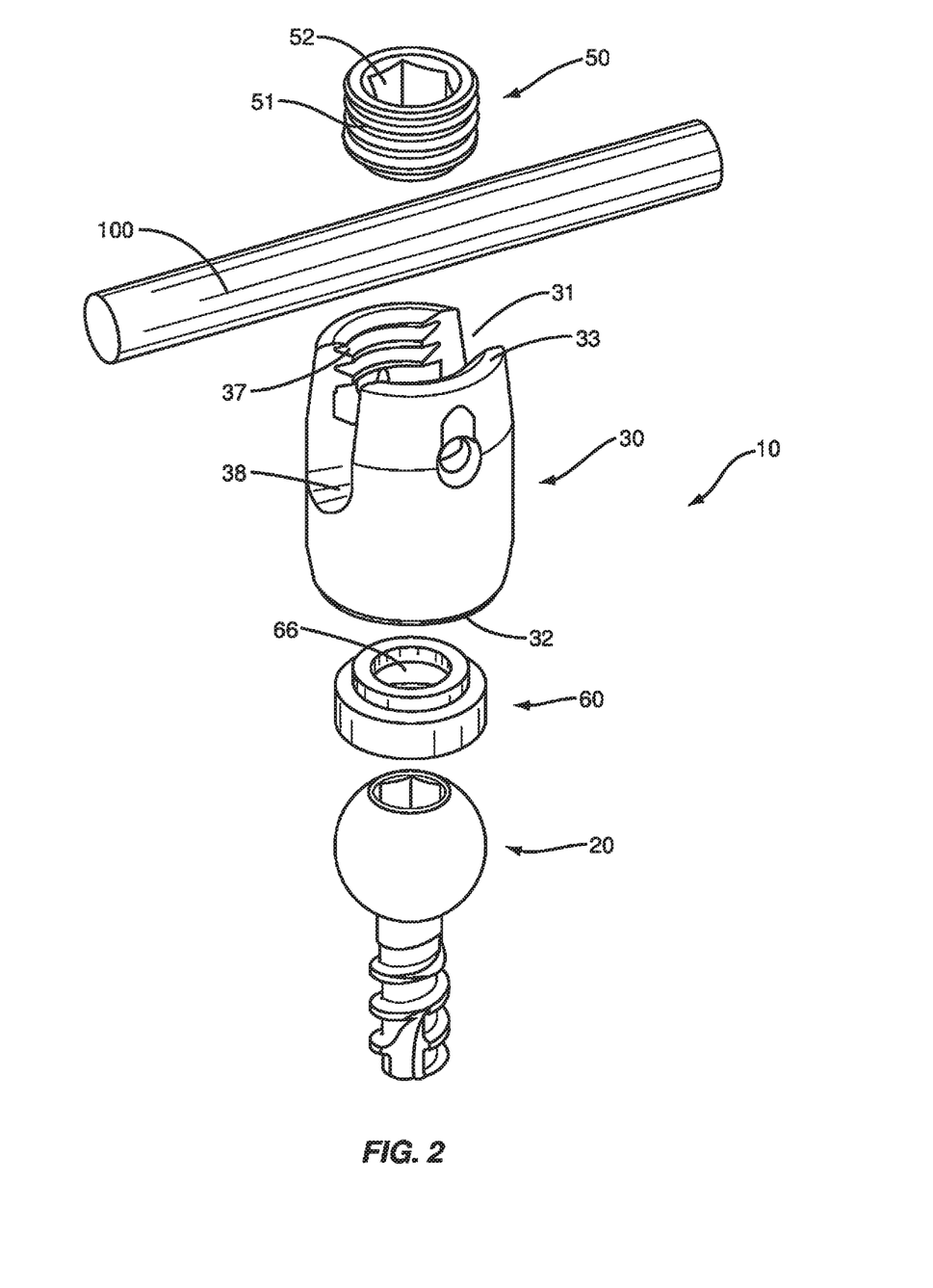
FIG. 2 illustrates an example exploded view of a screw assembly and longitudinal member.

FIG. 2 illustrates an example exploded view of a screw assembly and longitudinal member according to an embodiment. As shown by FIG. 2, anchoring member 30 provides a connection between the screw 20 and longitudinal member 100. Anchoring member 30 includes a first end 32 that faces towards the vertebral member 200, and a second end 33 that faces away. A chamber is positioned between the first and second ends 32, 33 and is sized to receive at least a portion of the screw 20. In various embodiments, a first end 32 may be considered a base portion of an anchoring member 30, and a second end 33 may be considered a head portion of an anchoring member.

The second end 33 of the anchoring member 30 includes a channel 31 sized to receive the longitudinal member 100. Channel 31 terminates at a lower edge 38 that may include a curved shape to approximate the longitudinal member 100. Threads 37 may be positioned towards the second end 33 to engage with the set screw 50. In one embodiment as illustrated in FIG. 2, the threads 37 are positioned on the interior of the anchoring member 30 facing towards the channel 31. In another embodiment, the threads 37 may be on the exterior of the anchoring member 30. An interior of the anchoring member 30 may be open between the first and second ends 32, 33.

In various embodiments, an anchoring member 30 may include a washer 60. A washer 60 may be generally cylindrical and may have a hole 66 therethrough. As illustrated by FIG. 1 a washer 60 may be positioned near a first end 32 of an anchoring member 30. A screw 20 may engage with an anchoring member 30 via positioning through the hole 66 of a washer 60. A washer 60 may include recessed portions which may be configured to accommodate placement of a longitudinal member 100 therein. The use of a washer 60 in connection with an anchoring member 30 may help minimize misalignment of the longitudinal member within the anchoring member.

In an embodiment, set screw 50 attaches to the anchoring member 30 and captures the longitudinal member 100 within the channel 31. As illustrated in FIG. 2, the set screw 50 may be sized to fit within the interior of the channel 31 and include exterior threads 51 that engage threads 37 on the anchoring member 30. A driving feature 52 may be positioned on a top side to receive a tool during engagement with the anchoring member 30. In some embodiments, the set screw 50 may be mounted on an exterior of the anchoring member 30. Set screw 50 includes a central opening and is sized to extend around the second end 33. A set screw 50 may be a break-off set screw or a non-break-off set screw. In certain embodiments, a set screw 50 may include a slot for receiving or routing of electronic connections. Threads 51 are positioned on an inner surface of the central opening to engage with the external threads 37 on the anchoring member 30. The set screw 50 and anchoring member 30 may be constructed for the top side of the set screw 50 to be flush with or recessed within the second end 33 when mounted with the anchoring member 30.

Figure 3A:
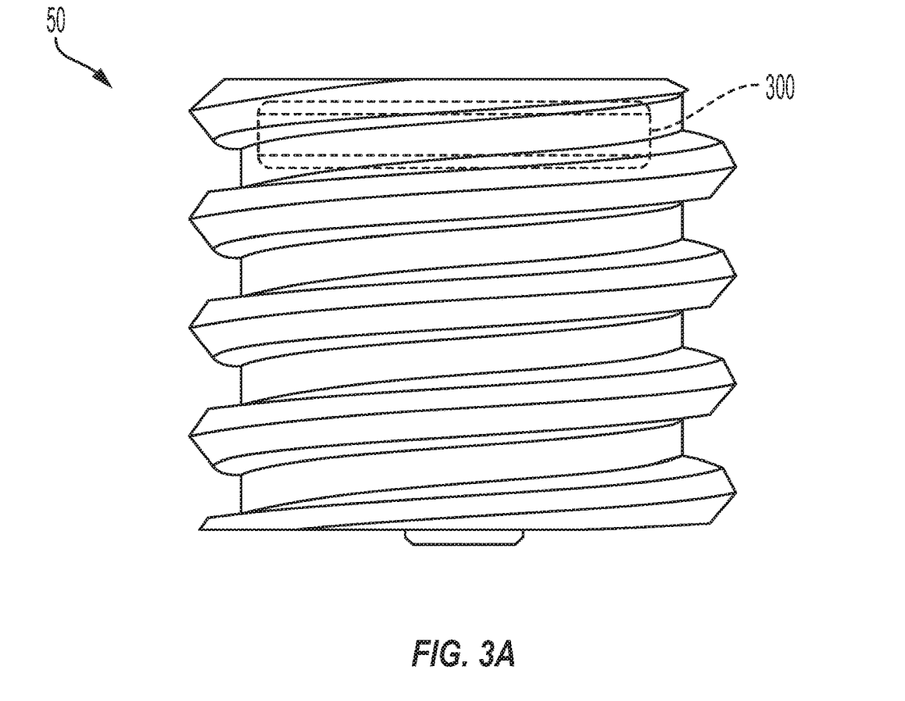
FIGS. 3A and 3B illustrate example antenna placements for an implant.
Figure 3B:
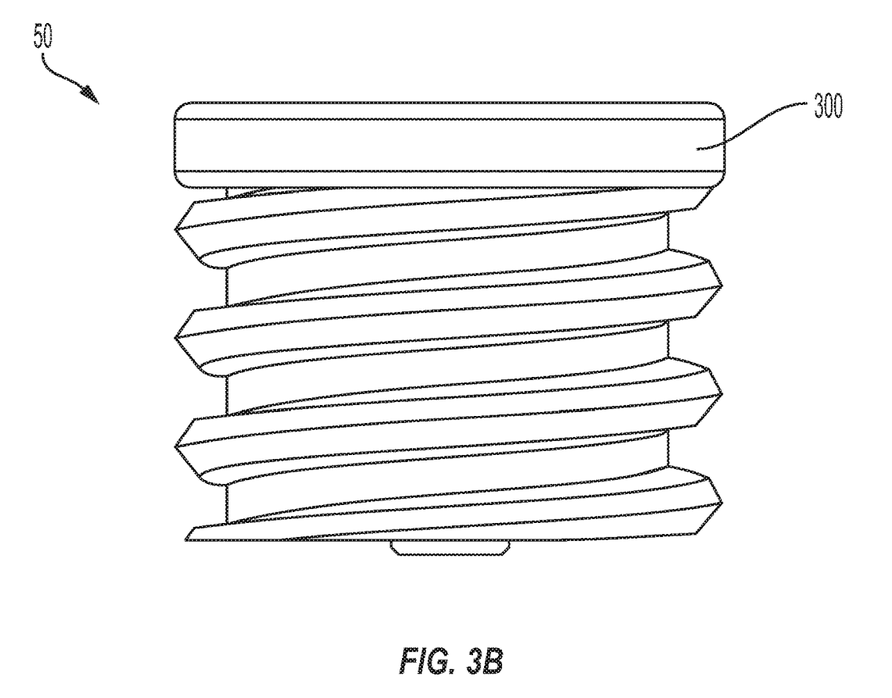

In various embodiments, an implant may have one or more antennas. FIG. 3A illustrates an example set screw 50 having an antenna 300 positioned on an external portion of the set screw. FIG. 3B illustrates an example set screw 50 having an antenna 300 positioned internally in a central opening of the set screw. Examples of an antenna 300 include, without limitation, a radio frequency identification (RFID) coil, a near field-communication (NFC) antenna or other short-range communication transmitter and/or receiver. Examples of antennae and example placements are described in U.S. patent application Ser. No. 16/395,221, filed Jul. 3, 2019, the contents of which are incorporated into this disclosure by reference it its entirety.

In various embodiments, an implant may include a control unit. A control unit may be part of a set screw, anchoring member, and/or the like. A control unit may include one or more integrated circuits or micro-electronic chips for powering implant and/or detecting/sensing diagnostics. Examples of integrated circuits or micro-electronic chips include, without limitation, an RFID chip, an NFC chip, and/or the like. In another embodiment, an integrated circuit may include a custom radio frequency communication scheme or protocol. An integrated circuit may include one or more components for powering the implant and/or detecting/sensing diagnostics, and is suitable for implantation. In some embodiments, an integrated circuit may include, for example, a flexible printed circuit.

In certain embodiments, an integrated circuit may transmit one or more measurements to the reader device. This transmission may occur in response to being interrogated by the reader device, or the transmission may be initiated by the integrated circuit. The reader device may receive the transmitted measurements, and may cause at least a portion of the measurements to be displayed to a user. For instance, a physician may use a reader device to interrogate a patient's implant. The reader device may include a display, or may be in communication with a display device, which may display at least a portion of the measurements received from the implant.

An integrated circuit may be passive, meaning that it has no internal power source and is powered by the energy transmitted from a reader device. With respect to an assembly having a passive integrated circuit, the integrated circuit may not transmit information until interrogated by a reader device.

In another embodiment, an integrated circuit may be active, meaning that the chip is battery-powered and capable of broadcasting its own signal. An active integrated circuit may transmit information in response to being interrogated by a reader device, but also on its own without being interrogated. For instance, an active integrated circuit may broadcast a signal that contains certain information such as, for example, one or more measurements gathered by an implant. An active integrated circuit may continuously broadcast a signal, or it may periodically broadcast a signal. Power may come from any number of sources, including, for example, thin film batteries with or without encapsulation or piezo electronics.

In some embodiments, the control unit may remotely communicate with electronic components disposed outside or external to a body of a patient. For instance, a control unit may include one or more transmitters and/or receivers for facilitating wireless communication with electronic components disposed outside or external to a body of a patient. In some embodiments, the control unit may remotely communicate with such external electronic components to power implant and/or transfer, transmit and/or receive data relating to implant including treatment and/or diagnostics, as described herein. In some embodiments, the remote communication can include a wireless link, such as, for example, Bluetooth, NFC, WiFi, MICS, and/or as described in U.S. Pat. No. 5,683,432 "Adaptive Performance-Optimizing Communication System for Communicating with an Implantable Medical Device" to Goedeke, et al., the contents of which being hereby incorporated by reference in its entirety.

A control unit may communicate with an external electronic device such as, for example, a reader device. For example, an RFID chip may be read by an RFID reader. As another example, an NFC chip may be read by or may otherwise communicate with an NFC reader or other NFC-enabled device. A reader device may interrogate an integrated circuit when in placed within a certain distance to the integrated circuit. In other embodiments, an integrated circuit may communicate with a reader or other electronic device without being interrogated.

Figure 4A:
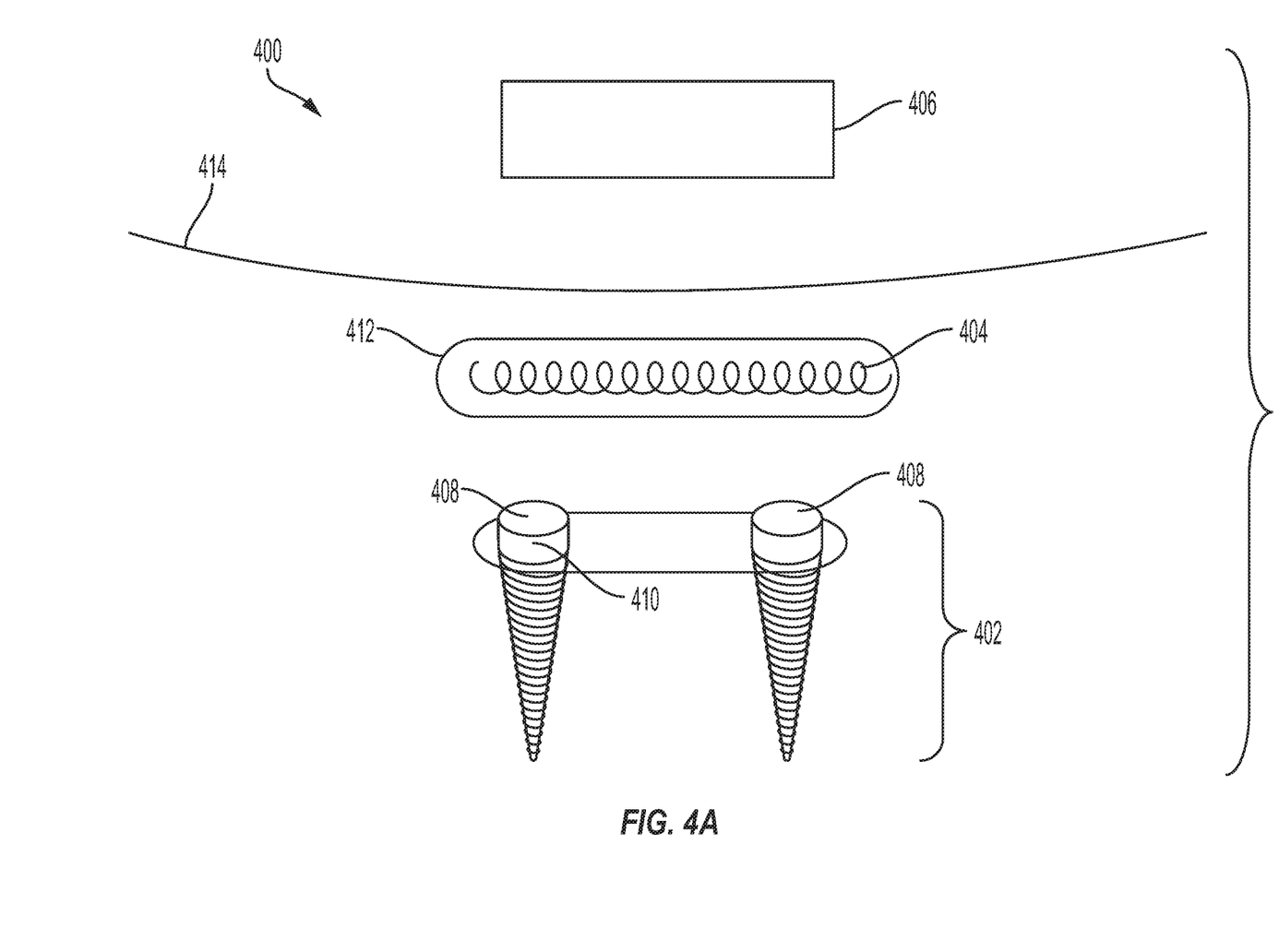
FIG. 4A illustrates an example energy transfer system for an implant.

FIG. 4A illustrates an example energy transfer system for an implant according to an embodiment. As illustrated by FIG. 4A, the system 400 may include an implant 402, a relay device 404, and a reader device 406. As illustrated in FIG. 4A, an implant 402 may have one or more antennae 408 and a control unit 410. The control unit 410 may be positioned within at least a portion of a set screw of a pedicle screw assembly according to an embodiment. Alternate positions of a control unit 410 may be used within the scope of this disclosure. FIG. 4A illustrates the implant 402 as a pedicle screw assembly. However, it is understood that additional and/or alternate types of implants may be used within the scope of this disclosure.

In various embodiments, a relay device 404 may be a transfer coil such as, for example, an induction coil. A relay device 404 may be fabricated from an electrical conductor such as, for example, wound copper. In various embodiments, a relay device may include a ferrite core, which may help to increase absorption of energy. Additional and/or alternate materials may be used within the scope of this disclosure.

A relay device 404 may wirelessly receive energy from a reader device 406, and may transfer at least a portion of the received energy to an antenna of an implant 402. In various embodiments, the received energy may include data. Similarly, a relay device 404 may receive data from an antenna 408 of an implant, and transfer at least a portion of the received data to a reader device 406. As such, a relay device 404 may act as a relay between a reader device 406 and an implant 402. In this way, a relay device 404 may bridge distance constraints between an implant 402 and an external power supply. In various embodiments, a reader device 406 may transfer energy to a relay device 404 when positioned within two to three inches from the relay device.

A relay device 404 may be positioned in a subcutaneous pocket 412 of a patient. The subcutaneous pocket 412 may be surgically created. In various embodiments, a relay device 404 may be positioned in subcutaneous pocket 412 that is located in proximity to an implant 402. For example, a relay device 404 may be positioned within a half an inch to three inches from an implant 402. Alternate distances or ranges of distances may be used within the scope of this disclosure. As another example, a relay device 404 may be positioned approximately halfway between an implant 402 and the surface 414 of a patient's skin. Additional and/or alternate placements and/or spacing of a relay device are within the scope of this disclosure.

In various embodiments, an implant 402 may be positioned approximately four inches below the skin of a patient. The distance between an implant 402 and a relay device 404 may be between a half an inch and three inches. The distance between a relay device 404 and a patient's skin may be approximately two to three inches. It is understood that alternate distances or ranges of distances may be used within the scope of this disclosure.

The reader device 406 may serve as a remote power source disposed outside or external to a body of a patient. The control unit of an implant 402 may be configured for inductive communication with the reader device 406 for power harvesting of a communication signal for powering implant. In some embodiments, reader device may include or be a component of a computer, a tablet, a smartphone, a cell phone, PDA, laptop, surgical instrument, clothing, accessory and/or other device.

The reader device 406 may emit a small electric current to create a magnetic field that bridges the physical space between the reader device and implant 402 implanted within a patient. The reader device 406 radiates energy through a cutaneous barrier, such as, for example, the skin 414 of a patient adjacent to the implant 402. An electromagnetic field may be generated by the reader device 406 (e.g., a transmitting coil) to transmit power across the skin 414 to the control unit of the implant 402. The control unit 410 may use the received energy to power or charge the implant 402. The received energy may include data being transmitted to the implant. The control unit 410 may receive the data from the energy. In various embodiments, the implant 402 may send data to the reader device 406. For example, the implant 402 may send data via one or more antennae of the implant to the relay device 404. The relay device 404 may in turn transmit the data to the reader device 406.

In some embodiments, the control unit 410 may include diagnostic sensor electronics connected with one or more sensors disposed about an implant to obtain and store data received from implant and surrounding tissue. Diagnostic sensor electronics may comprise various commercially available integrated circuit devices, see, for example, but not limited to, the AD5933 Impedance Converter Network Analyzer distributed by Analog Devices. Integrated circuit device may comprise various commercially available integrated circuit devices, see, for example, but not limited to, the RF430 microcontroller distributed by Texas Instruments RF430.

Figure 4B:
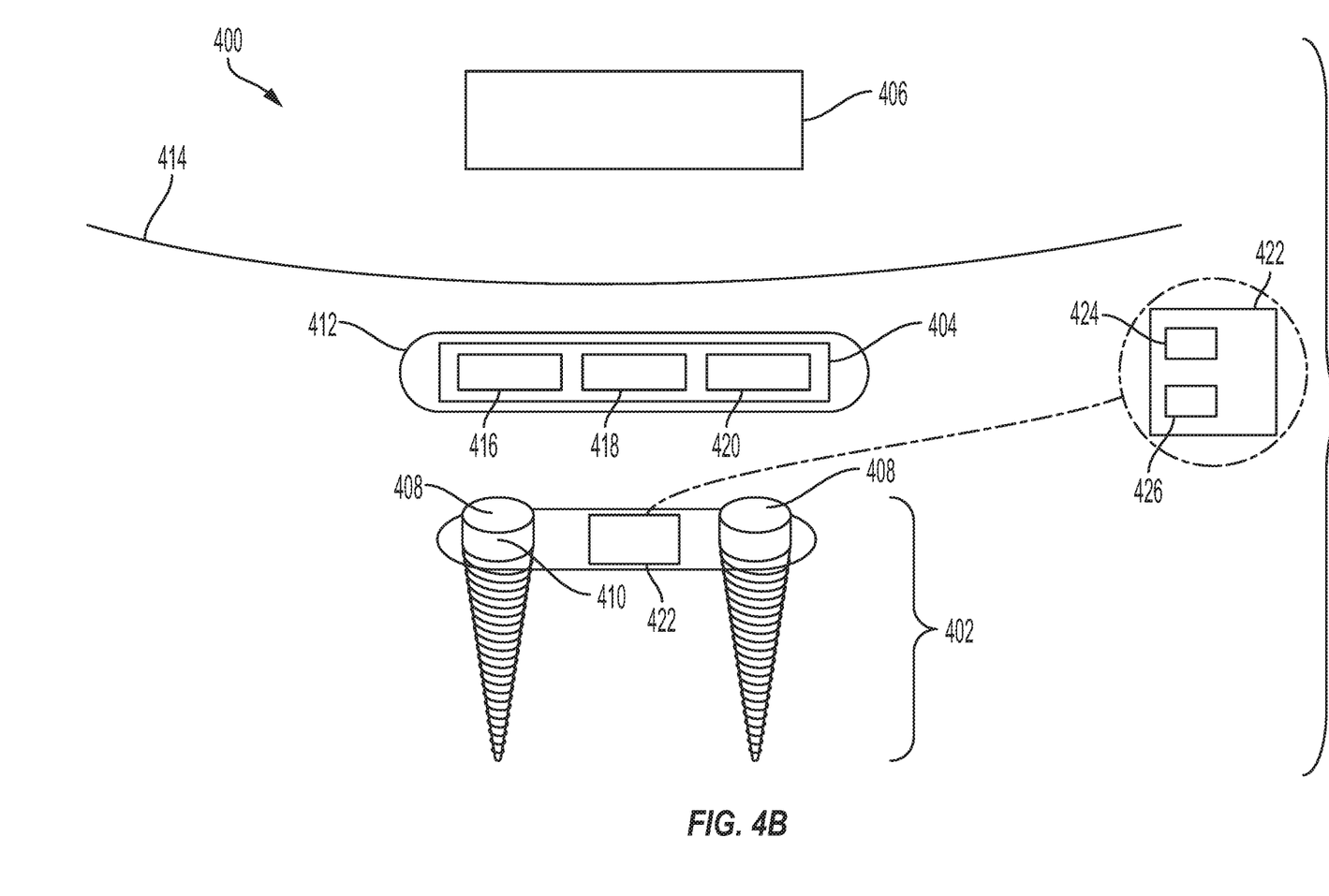
FIG. 4B illustrates an example energy transfer system for an implant.

FIG. 4B illustrates an alternative embodiment of an example energy transfer system for an implant according to an embodiment. As illustrated in FIG. 4B, a relay device 404 may include a battery 416. The battery 416 may be inductively powered or charged by an external device such as, for example, a reader device 406. A relay device 404 may include memory 418 and/or a communication device 420. A communication device 420 may facilitate communication, such as wireless communication, between the relay device 404 and one or more other devices disposed within or outside of the body of a patient. Examples of a communication device 420 may include, for example, an antenna, a receiver, a transmitter, a transceiver, an NFC chip, an RFID chip, and/or the like.

A reader device 406 may emit a small electric current to create a magnetic field that bridges the physical space between the reader device and relay device 404. The reader device 406 radiates energy through a cutaneous barrier, such as, for example, the skin 414 of a patient adjacent to the relay device 404. An electromagnetic field may be generated by the reader device 406 (e.g., a transmitting coil) to transmit power across the skin 414 to the relay device 404. The battery 416 of the relay device 404 may use the received energy to power or charge the relay device. The relay device 404 may transmit power to the implant 402. The received energy may include data being transmitted. The relay device 404 may receive the data from the energy. In various embodiments, the relay device 404 may send data to the reader device 406 and/or the implant 402. For example, the implant 402 may send data via one or more antennae of the implant to the relay device 404. The relay device 404 may in turn transmit the data to the reader device 406.

In various embodiments, data recorded by an implant 402 may be stored in the memory 418 of a relay device 404. This may allow extended recording of data from an implant 402 which may be downloaded at some future time such as, for example, at an office visit.

In various embodiments, a relay device 404 may be used in conjunction with an implant device 402 having one or more sensor devices 422. A sensor device 422 may include a battery 424 and or more sensors 426. A sensor device 422 may be configured to attach to a portion of an implant 402, such as, for example, a longitudinal member. A battery 424 of a sensor device 422 may be powered by a battery 416 of the relay device 404. The sensors 426 of a sensor device 422 may include, for example, a tri-axial accelerometer, a tri-axial gyroscope and/or the like. A sensor device 422 may collect data from one or more of its sensors 426 and may transmit at least a portion of this data to a relay device 404. The relay device 404 may store at least a portion of the received data in its memory 418. This data may be downloaded and/or otherwise transmitted from the relay to an external device.

Figure 5:
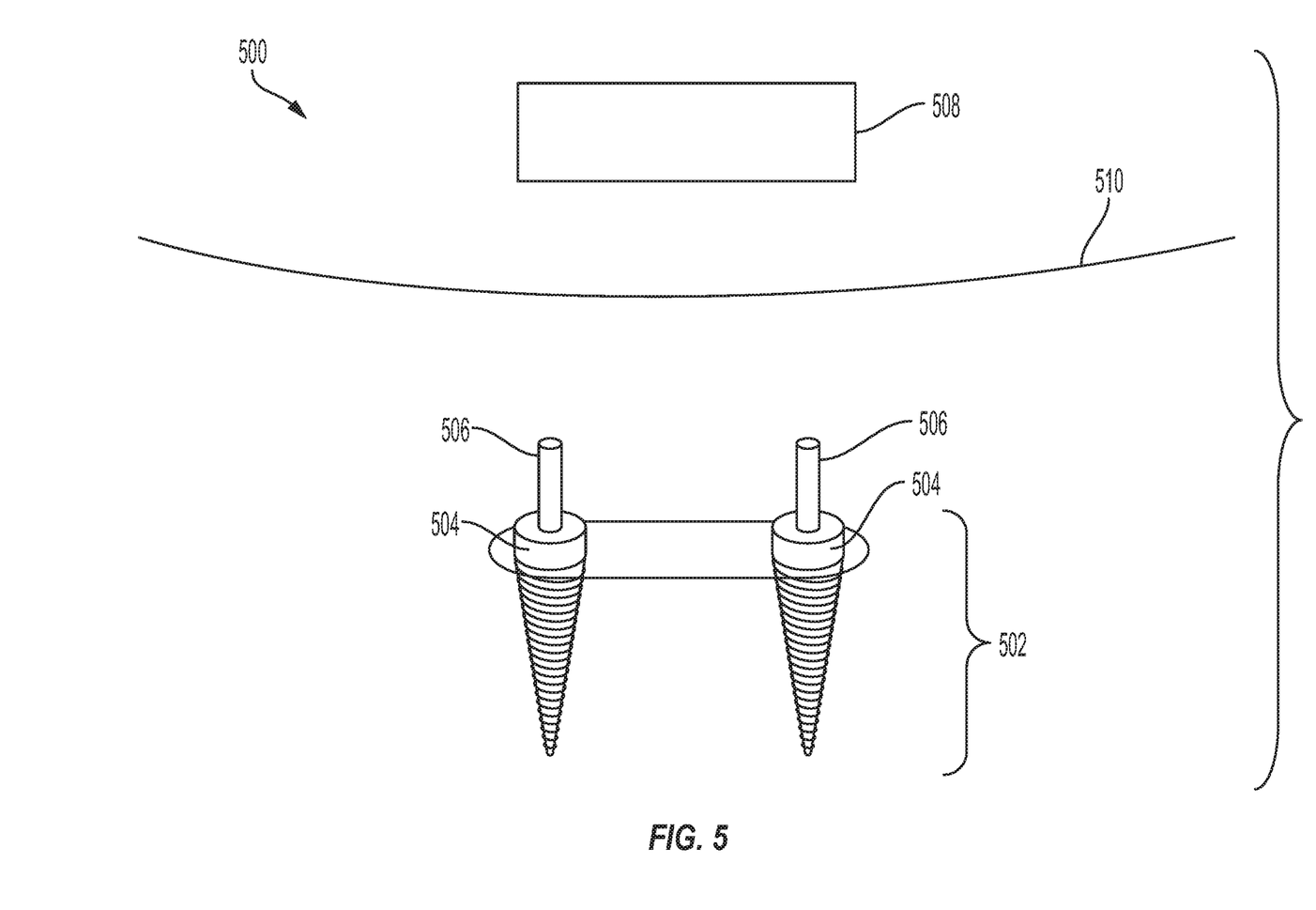
FIG. 5 illustrates an example energy transfer system for an implant.

FIG. 5 illustrates an example energy transfer system for an implant according to an embodiment. As illustrated by FIG. 5, the system 500 may include an implant 502 and a reader device 508. As illustrated in FIG. 5, an implant 502 may have one or more antennae 504 and a control unit 506. One or more of the antennae 504 may include an antenna extender 506 according to an embodiment. FIG. 5 illustrates the implant 502 as a pedicle screw assembly. However, it is understood that additional and/or alternate types of implants may be used within the scope of this disclosure.

An antenna extender 506 may be fabricated from a flexible, dielectric material such as, for example, a silicon substrate. The composition and flexible nature of an antenna extender 506 may reduce the risk that a patient will experience tissue irritation post operation.

An antenna extender 506 may be attached at a proximal end to a portion of an implant 502 that is in proximity to an antenna 504. For example, as illustrated by FIG. 5, an antenna extender may be attached to a set screw near a distal end of the set screw. An antenna extender may be attached to an implant in any suitable manner including, without limitation, laser welding.

A distal end of an antenna extender 506 may extend away from an implant 502, and toward the skin 510 of a patient. As such, the use of an antenna extender 506 may help to reduce the distance between the implant 502 and a reader device 508.

In various embodiments, as illustrated by FIG. 5, an implant 502 may include more than one antenna extender 506. For instance, referring to FIG. 5, an implant includes two antennae 504. An antenna extender 506 may be attached in proximity to each antenna. Although FIG. 5 illustrates the use of multiple antenna extenders 506, it is understood that more or fewer antenna extenders may be used within the scope of this disclosure.

In various embodiments, an antenna extender 506 may have a diameter that is compatible with a cannulated instrument driver. A cannulated instrument driver may be a tool having a cannula. A cannulated instrument driver may be used to position an implant or an implant component within a patient.

The length of an antenna extender may be between a half an inch and three inches in various embodiments. Alternate distances or distance ranges may be used within the scope of this disclosure. In some embodiments, an antenna extender may correspond to certain category of extenders such as, for example, short, medium, and long. Differently sized antenna extenders may be used based placement of an implant within a patient, a patient's anatomy and/or the like.

In various embodiments, a reader device 508 may transmit energy to the implant 502 via the antenna extenders 506. Similarly, the implant 502 may send data to the reader device 508 via the antenna extenders 506.

Figure 6A:
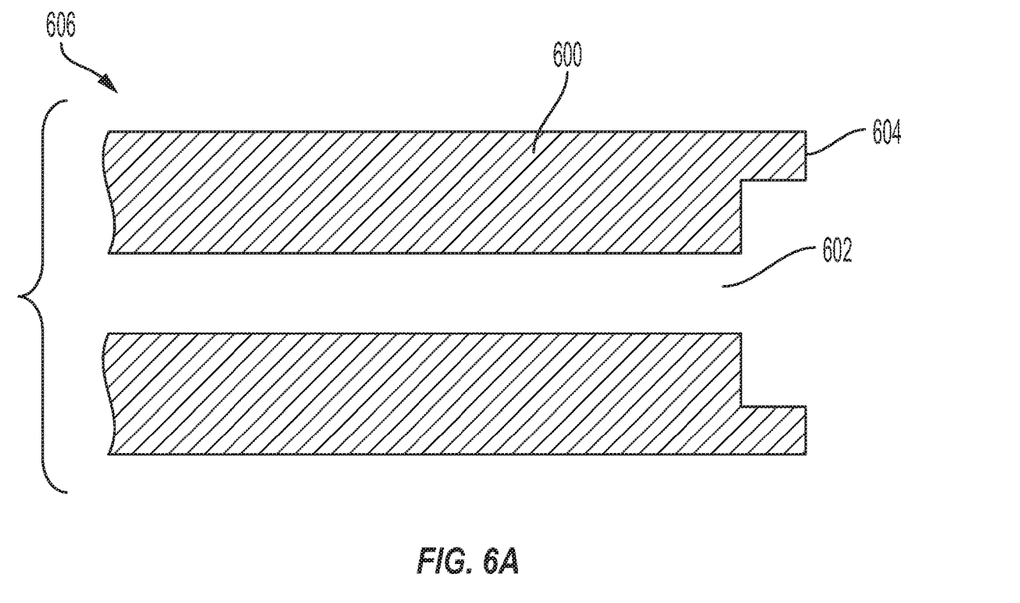
FIG. 6A illustrates an example cannulated instrument driver.

FIG. 6A illustrates a profile of an example cannulated instrument driver according to an embodiment. As illustrated by FIG. 6A, a cannulated instrument driver 600 has a cannula 602 that extends from a first end 604 of the cannulated instrument driver toward a second end 606 of the cannulated instrument driver.

Figure 6B:
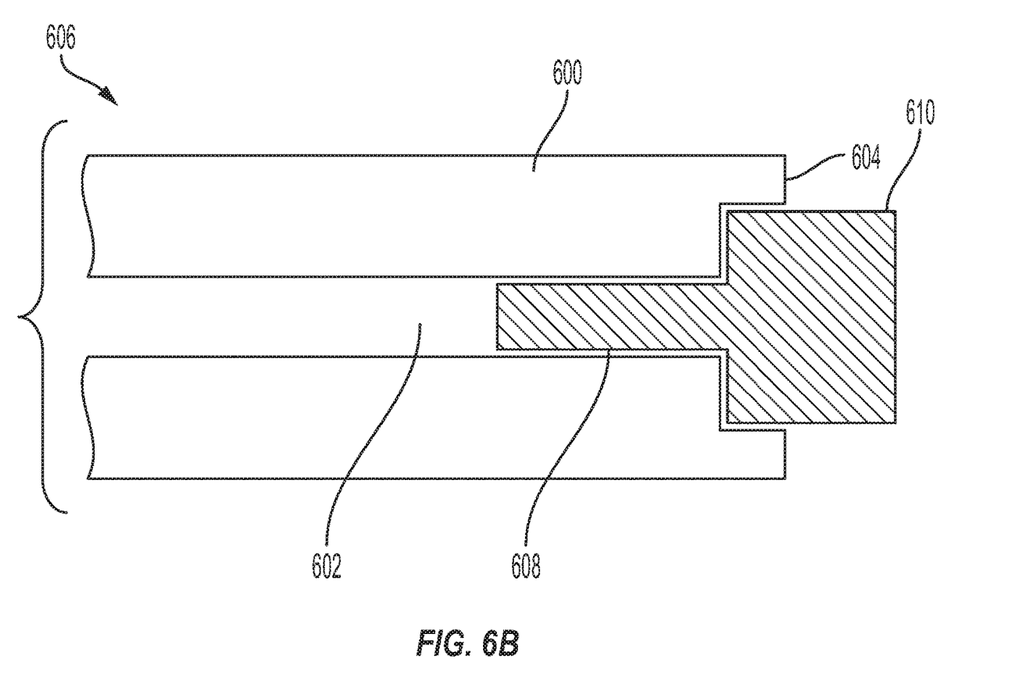
FIG. 6B illustrates an example cannulated instrument driver engaging an example set screw.

FIG. 6B illustrates an example cannulated instrument driver holding a set screw 610 for implantation according to an embodiment. As illustrated by FIG. 6B, an antenna extender 608 may be positioned within at least a portion of the cannula 602. The remaining portion of the set screw 610 may be positioned at one end of the cannulated instrument driver 600 and outside of the cannula 602. The cannula 602 may serve to protect an antenna extender 608 from damage during implantation. Once the set screw 610 is attached to an anchoring member, the cannulated instrument driver 600 may be retracted. Retraction of the cannulated instrument driver 600 may cause the antenna extender 608 to slide from the cannula 602.

Figure 7:
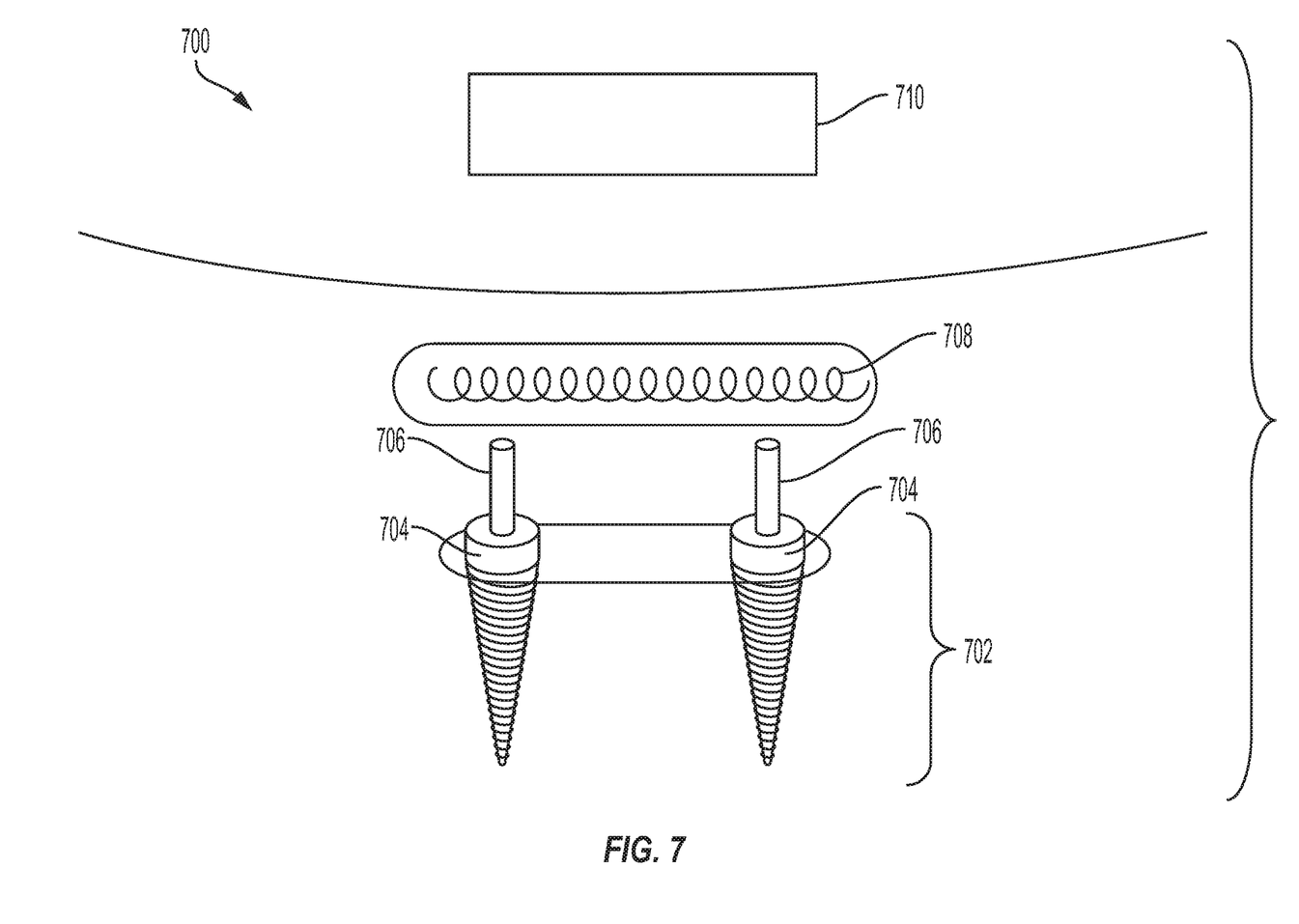
FIG. 7 illustrates an example energy transfer system for an implant.

In various embodiments, an energy transfer system may utilize a relay device and one or more antenna extenders, as illustrated by FIG. 7. As shown in FIG. 7, a system 700 may include an implant 702, one or more antennae 704, one or more antenna extenders 706, a relay device 708 and a reader device 710. The energy transfer system as illustrated by FIG. 7 may be utilized in connection with a relay device as described in connection with FIG. 4A, FIG. 4B, or a different relay device.

FIGS. 1-7 illustrate a multi-axial tulip-head pedicle screw according to various embodiments. However, it is understood that other types of anchoring members may be used within the scope of this disclosure. For example, fixed head screws or screws having differently shaped heads may be used. As another example, a hook member, a cross-link connector, an offset connector, or a hybrid hook-screw member may be used as well. Alternatively, non-anchoring members, such as, for example, an implant rigidly connected to a single rod, may be used within the scope of this disclosure.

The features and functions described above, as well as alternatives, may be combined into many other different systems or applications. Various alternatives, modifications, variations or improvements may be made by those skilled in the art, each of which is also intended to be encompassed by the disclosed embodiments.

The invention claimed is:

1. An energy transfer system comprising:
   a spinal implant having one or more antennae and one or more sensors, wherein the spinal implant is configured to be positioned within a spinal area of a patient;
   an antenna extender in proximity to at least one of the one or more antennae, the antenna extender extending away from the spinal implant toward the skin of the patient, the antenna extender comprising a flexible, dielectric material; and
   a relay device configured to be positioned within the patient between the antenna extender and the skin of the patient when implanted, wherein the relay device comprises memory,
   wherein the relay device is configured to receive energy from a reader device located externally to the patient and convey at least a portion of the received energy to the one or more antennae of the spinal implant,
   wherein the spinal implant is configured to transmit data collected by one or more of the one or more sensors to the relay device for storage in the memory.

2. The energy transfer system of claim 1, wherein the relay device further comprises a battery.

3. The energy transfer system of claim 1, wherein the relay device further comprises a communications device.

4. The energy transfer system of claim 1, wherein the one or more sensors are configured to attach to a longitudinal member of the spinal implant.

5. The energy transfer system of claim 1, wherein the relay device comprises an induction coil.

6. The energy transfer system of claim 1, wherein the relay device is configured to be positioned within a subcutaneous pocket.

7. The energy transfer system of claim 1, wherein the spinal implant is configured to be anchored to a vertebra of the patient.

8. The energy transfer system of claim 1, wherein the spinal implant comprises a pedicle screw having a set screw and an anchoring member and the set screw comprises the one or more antennae.

9. The energy transfer system of claim 1, wherein the spinal implant further comprises a control unit having one or more integrated circuits or micro-electronic chips.

10. The energy transfer system of claim 9, wherein the one or more integrated circuits comprises a flexible printed circuit.

11. The energy transfer system of claim 9, wherein the one or more micro-electronic chips comprises:
    a radio frequency identification chip; or
    a near field communication chip.

12. The energy transfer system of claim 1, wherein the spinal implant is configured to use the at least a portion of the received energy to power the spinal implant.

13. The energy transfer system of claim 1, wherein the spinal implant is configured to retrieve data from the received energy.

14. The energy transfer system of claim 1, wherein the relay device is further configured to receive information from the spinal implant and transfer at least a portion of the received information to the reader device.

* * * * *